United States Patent [19]

Slijkhuis et al.

[11] Patent Number: 5,298,398
[45] Date of Patent: Mar. 29, 1994

[54] PREPARATION OF 9-ALPHA-HYDROXY-17-KETO STEROIDS USING MYCOBACTERIUM SPECIES CBS 482.86

[75] Inventors: Harmen Slijkhuis, AE Berkel En Rodenrijs; Arthur F. Marx, GM Delft, both of Netherlands

[73] Assignee: Gist-Brocades NV, Delft, Netherlands

[21] Appl. No.: 925,107

[22] Filed: Aug. 6, 1992

Related U.S. Application Data

[60] Division of Ser. No. 729,892, Jul. 15, 1991, Pat. No. 5,166,055, which is a continuation of Ser. No. 289,057, Dec. 23, 1988, abandoned.

[30] Foreign Application Priority Data

Dec. 23, 1987 [EP] European Pat. Off. ........ 87202619.0

[51] Int. Cl.⁵ .................... C12N 1/20; C12P 33/00; C12P 33/06; C12P 33/02
[52] U.S. Cl. .................................. 435/52; 435/55; 435/56; 435/58; 435/61; 435/253.1
[58] Field of Search ............ 435/52, 55, 56, 61, 435/58, 253.1

[56] References Cited

U.S. PATENT DOCUMENTS

| | | | |
|---|---|---|---|
| 2,833,794 | 5/1958 | Goldkamp et al. | 435/61 |
| 3,487,907 | 1/1970 | Waard et al. | 435/55 |
| 3,684,657 | 8/1972 | Kraychy et al. | 435/55 |
| 3,759,791 | 9/1973 | Marsheck et al. | 435/55 |
| 4,035,236 | 7/1977 | Wovcha | 435/253 |
| 4,226,936 | 10/1980 | Wovcha et al. | 435/55 |
| 4,320,195 | 3/1982 | Hill et al. | 435/55 |
| 4,345,029 | 8/1982 | Wovcha et al. | 435/253 |
| 4,345,033 | 8/1982 | Wovcha et al. | 435/253.1 |
| 4,358,538 | 11/1982 | Wovcha et al. | 435/253.1 |
| 4,397,947 | 8/1983 | Marsheck et al. | 435/58 |
| 5,004,695 | 4/1991 | Bokany et al. | 435/55 |

FOREIGN PATENT DOCUMENTS

| | | |
|---|---|---|
| 0027829 | 5/1981 | European Pat. Off. . |
| 0263569 | 4/1988 | European Pat. Off. . |
| 322081 | 6/1989 | European Pat. Off. ............ 435/863 |
| 232167 | 1/1986 | Fed. Rep. of Germany ........ 435/55 |
| 26391 | 3/1978 | Japan ................................... 435/863 |
| 55-85397 | 6/1980 | Japan . |
| 85397 | 6/1980 | Japan ................................ 435/253.1 |
| 114187 | 6/1985 | Japan ................................... 435/863 |
| 6513718 | 4/1967 | Netherlands . |
| 6705450 | 10/1968 | Netherlands . |
| 2197869 | 6/1988 | United Kingdom . |

OTHER PUBLICATIONS

J. Org. Chem., vol. 44, No. 9, 1979, pp. 1582–1584.
J. Am. Chem. Soc., 80, 1958, p. 6148.

Primary Examiner—David M. Naff
Assistant Examiner—L. Blaine Lankford
Attorney, Agent, or Firm—Keck, Mahin & Cate

[57] ABSTRACT

9α-hydroxy-17-keto steroids are prepared by fermenting steroids having a C-17-side chain of 5–10 carbon atoms inclusive, with the novel *Mycobacterium species* CBS 482.86. Starting from various substrates containing a 5–10 C carbon chain on C-17, 9α-hydroxyandrost-4-ene-3,17-dione, 7α,9α,12α-trihydroxyandrost-4-ene-3,17-dione or 9α-hydroxyandrost-4,11-diene-3,17-dione is obtained in high yield. The resulting compounds are useful intermediates in the synthesis of therapeutically important steroids, particularly corticosteroids.

5 Claims, No Drawings

PREPARATION OF 9-ALPHA-HYDROXY-17-KETO STEROIDS USING *MYCOBACTERIUM* SPECIES CBS 482.86

This is a division of application Ser. No. 07/729,892, filed Jul. 15, 1991, now U.S. Pat. No. 5,166,055 which is a continuation of application Ser. No. 07/289,057, filed on Dec. 23, 1988, now abandoned.

The invention relates to a process for the preparation of 9α-hydroxy-17-keto steroids using a new microorganism of the genus Mycobacterium.

BACKGROUND OF THE INVENTION

It is well known that steroid molecules can be transformed by microorganisms (W. Charney, H. L. Herzog, Microbial Transformations of Steroids). Many processes using microbiological transformations of steroids have been developed, to replace cumbersome and expensive chemical processes. A cheap source for the preparation of useful steroid intermediates are the abundantly available sterols, for example cholesterol and sitosterol. Microorganisms have been selected which are able to use these steroids as a carbon source. In several patent publications, e.g. Dutch patent applications NL 6513718 and NL 6705450, the microbiological degradation of the C-17-side chain with the preservation of the steroid nucleus is described. With specific inhibitor compounds and later also with specially developed mutants, as described in U.S. Pat. Nos. 3,684,657, 3,759,791 or 4,345,029, it was possible to obtain in high yield androst-4-ene-3,17-dione and androsta-1,4-diene-3,17-dione, which are starting compounds for the synthesis of therapeutically useful steroids.

Among the microbiologically prepared steroids 9α-hydroxy-17-keto steroids are important because they are valuable starting compounds for the preparation of corticosteroids (J. Org. Chem. (1979) 44, 1582). The necessary introduction in prospective corticosteroids of a hydroxyl group on C-11 and optionally of a halogen atom on C-9 can be carried out by easy, well established chemical reactions, departing from this class of compounds.

A preferred compound of this type is 9α-hydroxyandrost-4-ene-3,17-dione, originally described in J. Amer. Chem. Soc. 80 (1958), 6148. It possesses anti-androgenic and anti-oestrogenic activity, but it is mainly used as an intermediate in the synthesis of therapeutically valuable corticosteroids (see e.g. European patent application EP-A-0263569).

In the following patent publications several methods are disclosed for obtaining 9α-hydroxy-17-keto steroids, particularly 9α-hydroxyandrost-4-ene-3,17-dione:

a. Microbiological introduction of the 9α-hydroxyl group starting from androst-4-ene-3,17-dione using e.g. a microorganism of the genus Nocardia (U.S. Pat. No. 4,397,947) or a *Corynespora cassicola* strain (European patent application EP-A-0027829).

b. U.S. Pat. No. 3,759,791 (examples 6 and 7) describes the presence of 9α-hydroxyandrost-4-ene-3,17-dione in the broth after the fermentation of sterols with a Mycobacterium strain. According to U.S. Pat. No. 4,035,236 *Mycobacterium fortuitum* NRRL B-8119 is able, though in a rather low yield, to degrade the C-17-side chain of sterols with the simultaneous introduction of the 9α-hydroxyl group. Besides the low yield, which is caused predominantly by the gradual further degradation of the desired product during incubation, a drawback of this process is that the microorganism is considered to be an opportunistic pathogen.

c. East German patent DD 232167 discloses the preparation of 9α-hydroxyandrost-4-ene-3,17-dione by the strain *Mycobacterium fortuitum* N10 (ZIMET 10849). According to a special feature the yield is raised to 40–50% by adding a finely dispersed, hydrophobic organic polymer to the fermentation medium.

d. The preparation of 9α-hydroxyandrost-4-ene-3,17-dione departing from sterols by using a Mycobacterium strain is also described in Japanese patent application JP 55/85397, but only a low yield is reported.

e. According to British patent application GB 2197869, published Jun. 2, 1988, production of 9α-hydroxyandrost-4-ene-3,17-dione is effected by sterol fermentation using a strain of the novel *Mycobacterium roseum* species. From 100 g sterol 28.5 g product is obtained.

THE INVENTION

The present invention provides a fermentation process, using a novel microorganism of the genus Mycobacterium, to convert steroids characterized by a C-17 carbon side chain, containing from 5–10 carbon atoms inclusive, into 9α-hydroxy-17-keto steroids and particularly, from various sterols, 9α-hydroxyandrost-4-ene-3,17-dione. This fermentation process can produce the desired steroids selectively and in high yield.

THE MICROORGANISM

The new Mycobacterium strain is obtained starting from a culture of Mycobacterium species NRRL-B-3805, which is described in U.S. Pat. No. 3,759,791. The Mycobacterium species URRL-B-3805 exhibits the general characteristics of *Mycobacterium vaccae,* as is apparent from U.S. Pat. No. 4,345,029, column 2, lines 34–40. Mycobacterium species NRRL-B-3805 converts sterols into androst-4-ene-3,17-dione in a high yield.

NRRL-B-3805 was subjected to a selection procedure by growing it f or many generations in media containing a mixture of β-sitosterol and androsta-1,4-diene-3,17-dione. The procedure eventually produced a novel strain which was designated as Mycobacterium species and deposited on Nov. 24, 1986 with the Central Bureau voor Schimmelcultures, P.O. Box 273, 3740 AG Baarn, The Netherlands under number CBS 482.86. The most conspicuous feature which distinguishes the new species from its parent strain Mycobacterium species NML-B-3805 is its ability to convert steroids stably into 9α-hydroxy steroids.

The new Mycobacterium species CBS 482.86 is clearly distinguished from the above-mentioned *Mycobacterium fortuitum* NRRL-B-8119 with regard to colour and form of colonies. With respect to biochemical properties they appear, when using the usual API-20B test assays, to possess a similarity of only about 75%. See further Table I. moreover, in contrast with said *Mycobacterium fortuitum* the novel Mycobacterium strain can produce a surprisingly high conversion, amounting to 80% of the sterol molecules. Moreover, under usual fermentation conditions, it does not further degrade the main product, 9-α-hydroxyandrost-4-ene-3,17-dione, which therefore accumulates in the fermentation liquor and is easily isolated in high yield by established procedures.

THE SUBSTRATES

For the preparation of 9α-hydroxy-17-keto steroids, the new Mycobacterium species is able to use various substrates, particularly steroids with a C-17-side chain having 5 to 10 carbon atoms, such as cholesterol, α₁- or β-sitosterol, stigmasterol, campesterol, ergosterol, cholic acid, lithocholic acid, 11,12-dehydro-lithocholic acid, and cholest-4-en-3-one. In the resulting fermentation liquor small amounts of by-products lacking the 9α-hydroxyl group may be found, e.g. 3-keto-delta-4 steroids or 3-keto-delta-1,4 steroids, some of which contain the hydroxyisopropyl group on C-17.

TABLE I

Characteristics of Mycobacterium species CBS 482.86, Mycobacterium species NRRL-B-3805 and *Mycobacterium fortuitum* NRRL-B-8119.

| API-20B test | M. species CBS 482.86 | M. species NRRL-B-3805 | M. fortuitum NRRL-B-8119 |
|---|---|---|---|
| gelatin-proteolysis | − | − | − |
| nitrites | − | − | + |
| β-galactosidase | − | − | − |
| acids from | | | |
| saccharose | − | − | − |
| L(+)arabinose | − | − | − |
| mannitol | + | + | − |
| fructose | + | + | + |
| glucose | + | + | + |
| maltose | − | − | − |
| starch | − | − | − |
| rhamnose | − | − | − |
| galactose | − | − | − |
| mannose | W | W | − |
| sorbitol | − | − | − |
| glycerol | + | + | + |
| indole | − | − | − |
| urease | − | − | + |
| H₂S-formation | − | − | − |
| acetoin | − | − | − |
| Simmons citrate | W | W | + |
| cytochrome oxidase | − | − | − |
| catalase | + | + | + |
| Growth at | | | |
| 37° C. | + | + | + |
| 40° C. | W | W | + |
| 45° C. | − | − | − |
| Growth on Mac Conkey agar | − | − | + |
| pigmentation | S | S | − |

−: negative; +: positive; W: weak; S: pigmentation even in dark (scotochromogenic).

Depending on the kind of substrate such by-products are e.g.:
androst-4-ene-3,17-dione,
androsta-1,4-diene-3,17-dione,
9α-hydroxy-20-hydroxymethylpregn-4-en-3-one.

Mixtures of the above-mentioned C-17-substituted steroids are also suitable substrates, e.g. the known mixture derived from soya containing 58% β-sitosterol, 5% campesterol and 25% stigmasterol, besides 12% other compounds. For the preparation of 9α-hydroxyandrost-4-ene-3,17-dione the preferred substrate is a sterol, especially β-sitosterol, but also lithocholic acid is suited. Various other C-17 substituted steroid substrates may be transformed to the corresponding 9α-hydroxy-17-keto steroids using the novel Mycobacterium strain.

THE PROCESS

The fermentation is carried out using methods well known in the art. The medium can be prepared with a growing culture of Mycobacterium species CBS 482.86 either by adding the selected steroid to the culture during the incubation period or by incorporating it in the nutrient medium prior to inoculation. The steroid substrate can be added singly or in combination with another steroid. The substrate can be added to the mixture either as a suspension or dissolved in a suitable organic solvent, e.g. dimethylformamide. The concentration of the steroid in the culture medium is preferably from 0.1 to 100 g/l, and more preferably 0.5–50 g/l. The culture is grown in a nutrient medium containing a carbon source such as an assimilable carbohydrate, and a nitrogen source such as an assimilable nitrogen compound e.g. a proteinaceous material. Preferred carbon sources include glucose, brown sugar, sucrose, glycerol, starch, particularly corn starch, lactose, dextrin and molasses. Preferred nitrogen sources include cornsteep liquor, yeast, autolyzed brewer's yeast with milk solids, soybean meal, cottonseed meal, corn meal, milk solids, pancreatic digest of casein, fish meal, distillers' solids, animal peptone liquors, meat and bone scraps and ammonium salts. It may be advantageous to use combinations of these carbon and nitrogen sources. Trace metals such as, for exampler, zinc, magnesium, manganese, cobalt and iron need not be added to the fermentation medium when tap water and unpurified ingredients are used as components of the medium prior to sterilization of the medium.

The transformation process to convert the substrate to the desired product is usually complete in 48 hours to 12 days. The incubation temperature during the process can range from 20° C. to 35° C. with 30° C. being preferred. The contents of the fermentation vessel are preferably aerated with sterilized air and agitated to facilitate growth of microorganism, thereby enhancing the effectiveness of the transformation process.

Upon completion of the transformation process, as shown by thin layer chromatography using silica gel plates (E. Merck, Darmstadt), the desired transformed steroid is recovered by means well known in the art. For example, the fermentation (transformation) reaction mixture, including the fermentation liquor and cells, can be extracted with a water-immiscible organic solvent for steroids. Suitable solvents include methylenechloride (preferred), chloroform, carbontetrachloride, ethylenechloride, trichloroethylene, diethylether, pentyl acetate, benzene and isobutylmethylketone.

Alternatively, the fermentation liquor and cells can first be separated by conventional methods, e.g. filtration or centrifugation, and then separately extracted with suitable solvents. The cells can be extracted with water-miscable or water-immiscible solvents. The fermentation liquor, freed from cells, can then be extracted by methods known in the art.

The extracts can be filtered through diatomaceous earth and the filtrate is distilled to dryness in vacuo. The resulting residue containing the desired transformed steroid may then be dissolved in 10% chloroform in methanol and concentrated subsequently with nitrogen on a steam bath until crystals appear. The solutions can then be cooled to room temperature and filtered to remove pure precipitated steroid. A further (crude) crop of the desired transformed steroid can be obtained by evaporation of the solvent from the remaining supernatant.

The progress of the transformation may be followed on thin layer plates, while quantative data may be obtained by separating a mixture of the culture liquid with methanol on a high performance liquid chromatography column. The structure of the resulting compounds may be confirmed by NMR analysis.

Instead of using the living Mycobacterium cells in the fermentation process the desired conversion may also be carried out with an enzyme preparation derived from cells of said Mycobacterium strain. A suitable preparation is one which contains the enzymes in an immobilized form which can be easily recovered.

Variants or mutants of the novel strain Mycobacterium species CBS 482.86 capable of effecting the same conversion are comprised as well by the invention.

The invention is further illustrated by the following examples which should, however, not be construed as a limitation of the invention.

In the examples the following abbreviations are used:

| AD | Androst-4-ene-3,11-dione |
| ADD | Androsta-1,4-diene-3,17-dione |
| 9-OH-AD | 9α-hydroxyandrost-4-ene-3,17-dione |
| 9-O-HMP | 9α-hydroxy-20-hydroxymethylpregn-4-en-3-one. |

EXAMPLE 1

Erlenmeyer flasks (500 ml) with 100 ml medium A were prepared.

| Medium A | |
|---|---|
| 10 g | Yeast extract (Difco) |
| 3.4 g | Potassium dihydrogen phosphate |
| 4.0 g | Tween 80 TM |
| 1000 ml | Distilled water |
| | pH adjusted to 7.0. |

The flasks were sterilized (20 minutes at 120° C.) and after cooling to 30° C. inoculated with a suspension of Mycobacterium species CBS 482.86. The inoculated medium was incubated at 30° C. for 48–72 hours on a rotary shaker at 280 rpm. Subsequently 10 ml of this culture was inoculated into 100 ml fresh medium A supplemented with cholesterol (100 mg). Cholesterol was added to medium A as a suspension, which was prepared as follows.

| A serum bottle (250 ml) containing | |
|---|---|
| 2.5 g | Cholesterol |
| 40 g | Glass beads (diameter 0.5 cm) |
| 50 g | Distilled water |
| 0.25 g | Tween 80 TM | was sterilized (20 minutes, 120° C.) and shaken on a rotary shaker (280 rpm) at room temperature for 200 hours. The inoculated mixture was incubated at 30° C. for 144 hours on a rotary shaker at 280 rpm. Following incubation, the culture was mixed with methanol and filtered. The filtrate was analyzed on HPLC. In the culture broth was identified

| 25 mg | 9-OH-AD |
| 6 mg | AD |
| 1 mg | ADD and |
| 1 mg | 9-OH-HMP. |

EXAMPLE 2

By substituting various steroids for cholesterol in the procedure of Example 1 9-OH-AD was produced as the main product. The yields are mentioned in Table II.

TABLE II

| mg substrate in 100 ml fermentation liquid | | mg product recovered using Mycobacterium species CBS 482.86 | | | |
|---|---|---|---|---|---|
| | | 9-OH-AD | AD | ADD | 9-OH-HMP |
| α-sitosterol | 100 | 30 | 2 | <1 | <1 |
| β-sitosterol | 100 | 50 | 1 | <1 | 1 |
| stigmasterol | 100 | 26 | 1 | <1 | <1 |
| campesterol | 100 | 45 | 1 | <1 | <1 |
| ergosterol | 100 | 30 | 1 | <1 | 1 |
| lithocholic acid | 100 | 12 | 11 | <1 | 1 |
| cholest-4-en-3-one | 100 | 26 | <1 | <1 | <1 |

EXAMPLE 3

The steroid substrates mentioned in the previous examples were added to the fermentation mixture in various combinations, e.g. the mixture of Example 5. The process was otherwise carried out as described in Example 1. The main produce was 9-OH-AD.

EXAMPLE 4

By substituting a cholesterol solution (50 mg in 2.5 ml ethanol) for the cholesterol suspension in Example 1 and following the Example 1 procedure, 9-OH-AD was obtained as the main product. Yields:

| 5 mg | 9-OH-AD |
| 2 mg | AD |
| <1 mg | ADD |
| <1 mg | 9-OH-HMP |

EXAMPLE 5

By substituting a solution (50 mg in 2.5 ml acetone) of a raw β-sitosterol mixture, consisting of β-sitosterol, campesterol and stigmasterol (in a ratio of approximately 10:5:1 and a total sterol content of 90%) for the cholesterol suspension in Example 1 and following the Example 1 procedure, 9-OH-AD was obtained as the main product. Yields:

| 13 mg | 9-OH-AD |
| 1 mg | AD |
| <1 mg | ADD |
| <1 mg | 9-OH-HMP |

EXAMPLE 6

By substituting cholic acid for the cholesterol suspension in Example 1 and following the Example 1 procedure, 7α,9α,12α-trihydroxyandrost-4-ene-3,17-dione was obtained as the main product, together with some minor products as shown by thin layer chromatography. The structure of the main product was confirmed by NMR analysis.

EXAMPLE 7

By substituting 11,12-dehydro-lithocholic acid for cholesterol in Example 1 and following the Example 1 procedure, 9α-hydroxyandrost-4,11-diene-3,17-dione is obtained as the main product, together with some minor products as shown by thin layer chromatography. The structure of the main product was confirmed by NMR analysis.

EXAMPLE 8

Medium A (500 ml in a 2000 ml Erlenmeyer flask) as described in Example 1 was inoculated with 10 ml of a fluid culture of Mycobacterium species CBS 482.86. The inoculated mixture was incubated at 30° C. for 48 hours on a rotary shaker at 200 rpm. This culture was used as the inoculum of a 10 l fermenter. The medium in the fermenter consists of

| 50 g | Yeast extract (Difco) |
|---|---|
| 20 g | Tween 80 TM |
| 2500 ml | Distilled Water |
| | pH adjusted to 6.8. |

The medium was sterilised (45 minutes at 120° C.), whereupon it was cooled to about 30° C. and then supplemented with potassium dihydrogen phosphate (17 g in 500 ml of distilled water) and ammonium sulphate (15 g in 500 ml of distilled water), both sterilised at 120° C. during 20 minutes. To this mixture, 2000 g of a suspension of the raw β-sitosterol mixture of Example 5 was added. The sterol suspension was prepared as follows:

| 4 serum bottles (2000 ml) each containing | |
|---|---|
| 25 g | Raw β-sitosterol |
| 200 g | Glass beads (diameter 0.5 cm) |
| 500 ml | Distilled water |
| 4 g | Tween 80 TM |

This mixture was sterilized at 120° C. during 45 minutes and then shaken at room temperature on a rotary shaker at 150 rpm for 400 hours. The inoculated mixture was grown n the stirred reactor (600 rpm) at 30° C., while sterile air was passed through the broth at a rate of 100 l/h and the pH was automatically kept at 7.0 with NH$_4$OH (5% in distilled water; sterilized by membrane filtration). After 72 hours a feed of Tween 80 TM (500 g made up with distilled water to 2500 g) was started at a rate of 15 g/h. The fermentation was then resumed for 216 hours whereupon the fermentation broth was extracted with methylene chloride. The extract was filtered through diatomaceous earth and the filtrate was vacuum distilled to dryness. The residue was taken up in 10% chloroform in methanol and then concentrated with nitrogen on a steam bath until crystals appear. The solution was then cooled to room temperature and filtered to remove the precipitated sterols. From the supernatant, on evaporation of solvent, crude 9-OH-AD crystal was obtained. The crude crystal contained (HPLC assay):

| 37.9 g | 9-OH-AD |
|---|---|
| 2.9 g | AD |
| <0.1 g | ADD |
| 0.2 g | 9-OH-HMP |

What is claimed is:
1. Process for the preparation of 9α-hydroxy-17-keto steroids comprising subjecting in an aqueous nutrient culture medium under aerobic fermentation conditions one or more steroid compounds having at least a C-17-carbon side chain containing from 5–10 carbon atoms inclusive, to the action of a C-17-side chain degrading microorganism or to one or more enzymes thereof to produce said steroid and recovering the 9α-hydro -17-keto steroid from the culture medium, wherein said microorganism is Mycobacterium species CBS 482.86, or a mutant thereof that produces said steroid under the same culture conditions as said microorganism.

2. Process according to claim 1, wherein the steroid compound is selected from the group consisting of $\alpha_1$- or β-sitosterol, stigmasterol, cholesterol, cholest-4-en-3-one, campesterol, ergosterol, cholic acid, lithocholic acid, 11,12-dehydrolithocholic acid and mixtures thereof.

3. Process according to claim 1, wherein the steroid prepared is 9α-hydroxyandrost-4-ene-3,17-dione and the steroid compound subjected to action by the microorganism is β-sitosterol.

4. Process according to claim 2, wherein the steroid prepared in 7α,9α, 12α-trihydroxyandrost-4-ene-3,17-dione and the steroid compound subjected to action by the microorganism is cholic acid.

5. Process according to claim 2, wherein the steroid prepared in 9α-hydroxyandrost-4 -ene-3,17,dione and the steroid compound subjected to action by the microorganism is 11,12-dehydrolithocholic acid.

* * * * *